US00PP15982P2

(12) United States Plant Patent
Horner

(10) Patent No.: US PP15,982 P2
(45) Date of Patent: Sep. 20, 2005

(54) ROSE PLANT NAMED 'HORCOHERENT'

(50) Latin Name: *Rosa hybrida*
Varietal Denomination: Horcoherent

(75) Inventor: Colin Peter Horner, Stansted (GB)

(73) Assignee: Spring Meadow Nursery, Inc., Grand Haven, MI (US)

( * ) Notice: Subject to any disclaimer, the term of this patent is extended or adjusted under 35 U.S.C. 154(b) by 20 days.

(21) Appl. No.: 10/882,872

(22) Filed: Jul. 1, 2004

(51) Int. Cl.[7] ..... A01H 5/00
(52) U.S. Cl. ..... Plt./102
(58) Field of Search ..... Plt./102, 106, 107, Plt./141

*Primary Examiner*—Anne Marie Grunberg
*Assistant Examiner*—June Hwu
(74) *Attorney, Agent, or Firm*—C. A. Whealy

(57) ABSTRACT

A new and distinct cultivar of Rose plant named 'Horcoherent', characterized by its low spreading plant habit; glossy dark green-colored leaflets; orange, pink and yellow-colored double flowers; resistance to Black Spot and mildews; and good garden performance.

2 Drawing Sheets

Botanical classification/cultivar designation: *Rosa hybrida* cultivar Horcoherent.

BACKGROUND OF THE INVENTION

The present Invention relates to a new and distinct cultivar of Rose plant, botanically known as *Rosa hybrida*, commercially used as cut stems with fruits or hips, and hereinafter referred to by the name 'Horcoherent'.

The new Rose is a product of a planned breeding program conducted by the Inventor in Stansted, Essex, United Kingdom. The objective of the breeding program was to develop new shrub Rose varieties with winter hardiness, disease resistance and attractive flower coloration.

The new cultivar originated from a cross-pollination made by the Inventor in 1994 of the Rose cultivar Flower Carpet, disclosed in U.S. Plant Pat. No. 7,282, as the female, or seed, parent with the Rose cultivar Scrivluv, not patented, as the male, or pollen, parent. The cultivar Horcoherent was discovered and selected by the Inventor in 1995 as a single flowering plant within the progeny of the stated cross-pollination in a controlled environment in Stansted, Essex, United Kingdom.

Asexual reproduction of the new Rose by softwood cuttings at Stansted, Essex, United Kingdom since 1995, has shown that the unique features of this new Rose are stable and reproduced true to type in successive generations of asexual reproduction.

SUMMARY OF THE INVENTION

The following traits have been repeatedly observed and are determined to be the unique characteristics of 'Horcoherent'. These characteristics in combination distinguish 'Horcoherent' as a new and distinct cultivar:

1. Low spreading plant habit.
2. Glossy dark green-colored leaflets.
3. Orange, pink and yellow-colored double flowers.
4. Resistant to Black Spot and mildews.
5. Good garden performance.

Plants of the new Rose are most similar to plants of the parent cultivars. Compared to plants of the female parent, the cultivar Flower Carpet, plants of the new Rose flower earlier and differ in flower color as plants of the cultivar Flower Carpet have pink-colored flowers. Plants of the new Rose and the male parent, the cultivar Scrivluv, differ in flower form and color as plants of the cultivar Scrivluv have yellow-colored single flowers.

Plants of the new Rose can be compared to plants of the Rose cultivar Flower Carpet Appleblossom, disclosed in U.S. Plant Pat. No. 10,239. Plants of the new Rose differ from plants of the cultivar Flower Carpet Appleblossom in time to flower and flower color as plants of the new Rose flower earlier than cultivar Flower Carpet Appleblossom and have darker pink-colored flowers.

BRIEF DESCRIPTION OF THE PHOTOGRAPHS

The accompanying colored photographs illustrate the overall appearance of the new Rose, showing the colors as true as it is reasonably possible to obtain in colored reproductions of this type. Colors in the photographs may differ slightly from the color values cited in the detailed botanical description which accurately describe the colors of the new Rose.

The photograph on the first sheet comprises a side perspective view of a typical plant of 'Horcoherent'.

The photograph on the second sheet is a close-up view of a typical flower of Horcoherent.

DETAILED BOTANICAL DESCRIPTION

The new Rose has not been observed under all possible environmental conditions. The phenotype may vary somewhat with variations in environment such as temperature and light intensity, without, however, any variance in genotype.

The aforementioned photographs, following observations and measurements describe plants grown in Grand Haven, Mich., in an outdoor nursery and under commercial production practices. Plants were about four years old. The photographs and description were taken during the late summer. In the following description, color references are made to The Royal Horticultural Society Colour Chart, 1995 Edition, except where general terms of ordinary dictionary significance are used.

Botanical classification: *Rosa hybrida* cultivar Horcoherent.

Parentage:

*Female, or seed, parent.*—*Rosa hybrida* cultivar Flower Carpet, disclosed in U.S. Plant Pat. No. 7,282.

*Male, or pollen, parent.*—*Rosa hybrida* cultivar Scrivluv, not patented.

Propagation:

*Type.*—Softwood cuttings.

*Time to initiate roots.*—About 12 days at 25° C.

*Time to produce a rooted young plant.*—About three months at 25° C.

*Root description.*—Freely branching; medium thickness; soft brown in color.

Plant description:

*Plant form.*—Low spreading perennial shrub.

*Growth habit.*—Vigorous growth habit. Freely branching habit; about 21 lateral branches per plant; dense and bushy growth habit.

*Plant height.*—About 40 cm.

*Plant width* (*spread*).—About 1 meter.

*Lateral branches.*—Length: About 40 cm. Diameter: About 4 mm. Internode length: About 4.5 cm. Strength: Strong. Angle: About 25 to 30° from vertical. Texture: Smooth, glabrous. Color: 138A. Thorns: Density: Moderate. Shape: Triangular with sharp acuminate apices. Height: About 7 mm. Diameter, at base: About 3 mm. Color: 181A.

*Foliage description.*—Leaves alternate; compound with about seven leaflets. Leaf length: About 2.5 cm. Leaflet width: About 1.5 cm. Leaflet shape: Ovate. Leaflet apex: Acute. Leaflet base: Obtuse. Leaflet margin: Serrate. Leaflet texture, upper and lower surfaces: Smooth, glabrous. Leaflet venation pattern: Pinnate. Leaflet color: Developing leaflets, upper surface: 136D. Developing leaflets, lower surface: 138A. Fully expanded leaflets, upper surface: 139A; glossy. Fully expanded leaflets, lower surface: 138B. Venation, upper surface: 139A. Venation, lower surface: 138B. Leaf petiole: Length: About 1.1 cm. Diameter: About 6 mm by 3 mm. Texture, upper and lower surfaces: Smooth, glabrous. Color, upper and lower surfaces: 144A.

Flower description:

*Flower type and habit.*—Orange and pink-colored double rotate flowers arranged singly or in terminal clusters with about five flowers per cluster. Flowers not persistent. Flowers face mostly outwardly.

*Natural flowering season.*—Plants flower in the landscape from May until frost in Grand Haven, Mich.; during this period flowering recurrent.

*Postproduction longevity.*—Flowers typically last one to two weeks on the plant as well as a cut flower.

*Fragrance.*—Slightly fragrant; typical of *Rosa*; sweet, pleasant.

*Flower buds.*—Height: About 2 cm. Diameter: About 8 mm. Shape: Ovoid. Color: 184D.

*Flowers.*—Diameter: About 5.1 cm. Depth: About 2.5 cm.

*Petals.*—Quantity per flower: About 18 in several whorls. Length: About 2.5 cm. Width: About 1.5 cm. Shape: Obovate. Apex: Obtuse with a cuspidate tip. Base: Attenuate. Margin: Entire. Texture, upper and lower surfaces: Smooth, glabrous. Color: Developing, upper surface: Towards the apex, 31C; towards the base, 12A. Developing, lower surface: Towards the apex, 23C; towards the base, 12A. Fully expanded, upper surface: Towards the apex, 54C; towards the base, 12A. Color becoming closer to 49C towards the apex. Fully expanded, lower surface: Towards the apex, 23C; towards the base, 12A.

*Sepals.*—Quantity per flower: Five. Length: About 2.3 cm. Width: About 6 mm. Shape: Lanceolate. Apex: Aute. Base: Fused. Margin: Entire. Texture, upper and lower surfaces: Smooth. Color: Developing, upper surface: 143C. Developing, lower surface: 143B. Fully expanded, upper surface: 143C. Fully expanded, lower surface: 143A.

*Peduncles.*—Length: About 4 cm. Diameter: About 2.5 mm. Orientation: About 20° from vertical. Strength: Strong. Color: 143A.

*Reproductive organs.*—Stamens: Quantity per flower: About 29. Anther shape: Oblong. Anther length: Less than 1 mm. Anther color: 22C. Pollen amount: Moderate. Pollen color: 22C. Pistils: Quantity per flower: About 30. Pistil length: About 1.5 mm. Stigma shape: Oval. Stigma color: 14B. Style length: About 5 mm. Style color: 14B. Ovary color: 143C.

*Fruits.*—Quantity per plant: About 110. Type: Fleshy hip. Shape: Roughly ovoid. Length: About 1.4 cm. Diameter: About 1 cm. Texture: Smooth, glabrous. Color: 143B.

*Seeds.*—Quantity per fruit: About six. Length: About 4 mm. Diameter: About 3.5 mm. Color: 149D.

Pathogen/pest resistance: Plants of the new Rose have been observed to be resistant to Black Spot and mildews. Plants of the new Rose have not been observed to be resistant to pests and other pathogens common to Roses.

Garden performance: Plants of the new Rose have been observed have good garden performance and to tolerate rain, wind and temperatures ranging from –25 to 30° C.

It is claimed:

1. A new and distinct cultivar of Rose plant named 'Horcoherent', as illustrated and described.

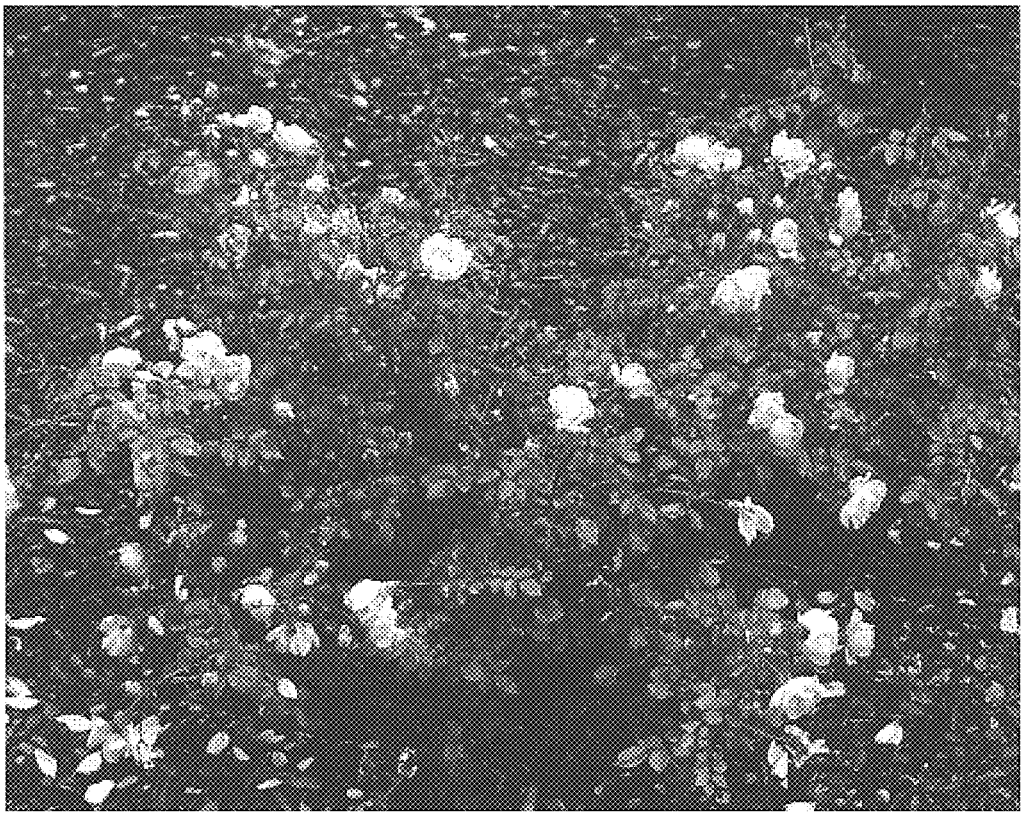

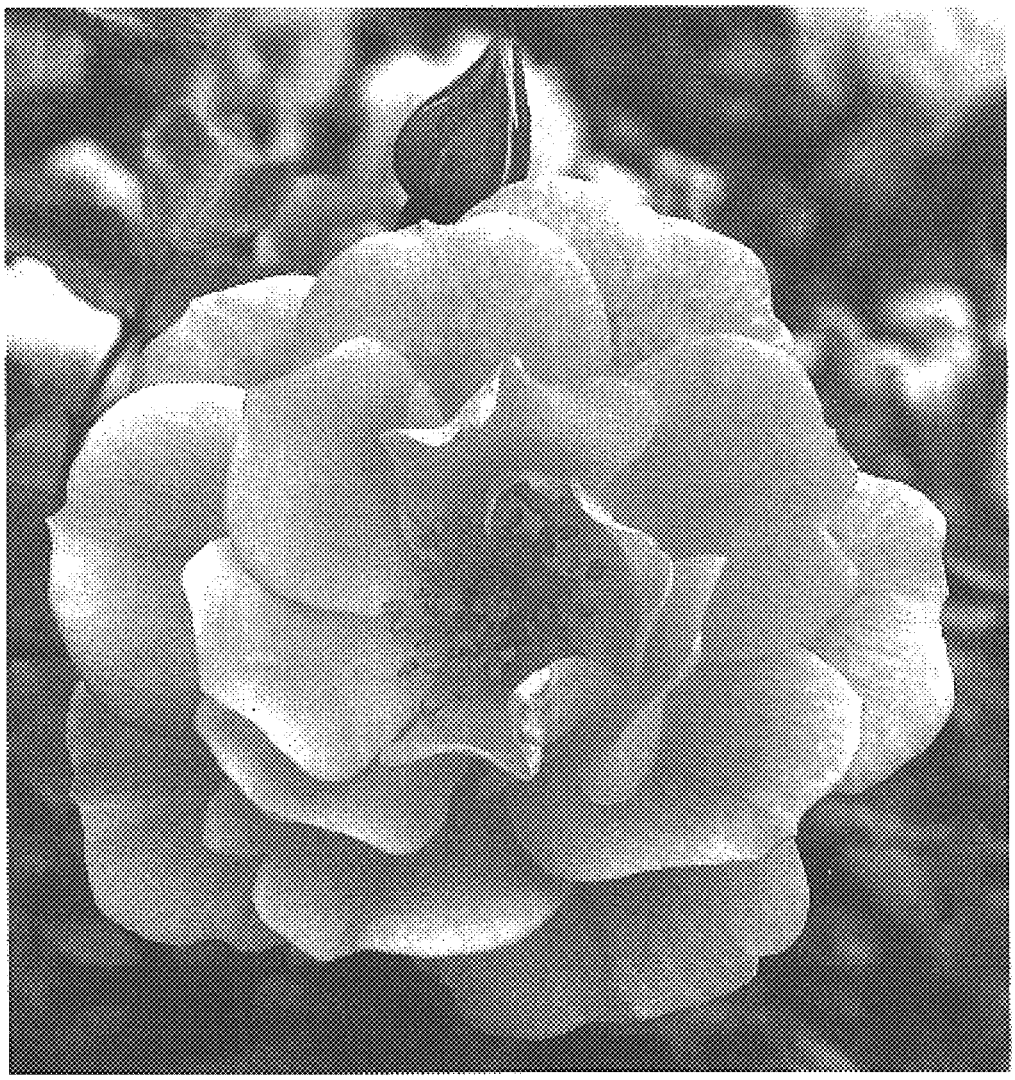

* * * * *